United States Patent
Yamamoto et al.

(10) Patent No.: US 10,549,038 B2
(45) Date of Patent: Feb. 4, 2020

(54) SYRINGE

(71) Applicant: DAICEL CORPORATION, Osaka (JP)

(72) Inventors: Yuzo Yamamoto, Hyogo (JP); Takatoshi Miyashita, Hyogo (JP)

(73) Assignee: Daicel Corporation, Osaka (JP)

( * ) Notice: Subject to any disclaimer, the term of this patent is extended or adjusted under 35 U.S.C. 154(b) by 163 days.

(21) Appl. No.: 15/638,211

(22) Filed: Jun. 29, 2017

(65) Prior Publication Data

US 2019/0001062 A1    Jan. 3, 2019

(51) Int. Cl.
| | |
|---|---|
| *A61M 5/20* | (2006.01) |
| *A61M 5/30* | (2006.01) |
| *A61M 5/31* | (2006.01) |
| *A61M 5/315* | (2006.01) |

(52) U.S. Cl.
CPC ............ *A61M 5/2046* (2013.01); *A61M 5/30* (2013.01); *A61M 5/315* (2013.01); *A61M 5/3129* (2013.01); *A61M 2005/3101* (2013.01); *A61M 2205/0216* (2013.01)

(58) Field of Classification Search
CPC .... A61M 5/2046; A61M 5/30; A61M 5/3129; A61M 5/315; A61M 5/3015; A61M 5/2053; A61M 5/20; A61M 5/3101; A61M 2205/0216; H01H 39/00; F15B 15/19
USPC .......................................................... 604/69
See application file for complete search history.

(56) References Cited

U.S. PATENT DOCUMENTS

| | | | |
|---|---|---|---|
| 3,802,430 A | * | 4/1974 | Schwebel ............... A61M 5/30 604/69 |
| 4,111,221 A | | 9/1978 | Olsen |
| 5,113,108 A | | 5/1992 | Yamashita et al. |
| 6,397,595 B2 | | 6/2002 | Benoit et al. |
| 6,556,119 B1 | | 4/2003 | Lell |
| 8,133,494 B2 | | 3/2012 | zur Megede et al. |

(Continued)

FOREIGN PATENT DOCUMENTS

| | | |
|---|---|---|
| JP | 2004-532049 A | 10/2004 |
| JP | 2005-523679 A | 8/2005 |

(Continued)

OTHER PUBLICATIONS

Office Action dated Mar. 9, 2018 in related U.S. Appl. No. 15/638,170, in 32 pages.

*Primary Examiner* — Kevin C Sirmons
*Assistant Examiner* — Leah J Swanson
(74) *Attorney, Agent, or Firm* — Knobbe Martens Olson & Bear LLP (57) ABSTRACT

A syringe transmits energy for injection satisfactorily to an injection objective substance while preventing influences of combustion products produced by the combustion of powder on the injection objective substance. A first piston part has a specific end face that receives ejection energy. A sealing member confines the combustion products in a first space separated by the sealing member. The sealing member has a fixed end portion and a contact portion that is in contact with the specific end face. In a state before the combustion of powder in an igniter, the contact portion is located at an initial position. With the combustion of powder in the igniter, the contact portion shifts to an ejection position with the sliding motion of the first piston part while being in contact with the specific end portion.

8 Claims, 5 Drawing Sheets

(56) References Cited

U.S. PATENT DOCUMENTS

| | | |
|---|---|---|
| 2004/0015125 A1 | 1/2004 | Alexandre et al. |
| 2004/0112239 A1 | 6/2004 | Parks et al. |
| 2005/0034595 A1 | 2/2005 | Kordel et al. |
| 2006/0281175 A1 | 12/2006 | McSwiggen et al. |
| 2008/0132450 A1 | 6/2008 | Lee et al. |
| 2010/0040619 A1 | 2/2010 | Li et al. |
| 2014/0061161 A1 | 3/2014 | Nakamura et al. |
| 2017/0314582 A1* | 11/2017 | Lell .................... A61M 5/2046 |
| 2017/0343021 A1 | 11/2017 | Yamada et al. |

FOREIGN PATENT DOCUMENTS

| | | |
|---|---|---|
| JP | 2007-525192 A | 9/2007 |
| JP | 2008-508881 A | 3/2008 |
| JP | 2008-206477 A | 9/2008 |
| JP | 2010-503616 A | 2/2010 |
| JP | 2014-049300 A | 3/2014 |
| WO | WO 2016/062304 A1 | 4/2016 |
| WO | WO-2016062304 A1 * | 4/2016 .......... A61M 5/2046 |

\* cited by examiner

SYRINGE

TECHNICAL FIELD

The present disclosure relates to a syringe that is used to inject an injection objective substance (i.e. a substance to be injected) to an injection target area of a target object.

BACKGROUND ART

Whether with or without a needle, injection syringes are configured to apply pressure to injection solution to inject the injection solution. Some needleless syringes that carry out needleless injection use an explosive as a pressure source (see e.g. Patent Literature 1). The needleless syringe disclosed in Patent Literature 1 is provided with a primer (or detonator) and a pyrotechnic charge. The primer is struck by a firing hammer to explode, so that the thermal energy of the explosion is transferred to the pyrotechnic charge. Consequently, the pyrotechnic charge burns to apply pressure to the injection solution. As the pyrotechnic charge, a single powder based on nitrocellulose is used.

The energy of combustion of powder is used as a power source for pressurization in fields other than syringes also. For instance, Patent Literature 2 discloses a technology relating to an actuator that interrupts the flow of medium in a fluid channel by driving a control member through a membrane using the energy of combustion of powder. In this technology, an elastically deformable membrane set between a control member and a housing is deformed by the pressure generated by the combustion of powder, so that a cylinder part attached to the film deforms to drive the control member.

PRIOR ART LITERATURES

Patent Literatures

Patent Literature 1: Japanese Translation of PCT International Application Publication No. 2004-532049
Patent Literature 2: U.S. Pat. No. 6,397,595

SUMMARY

Problems to be Solved

When utilizing the energy of combustion of powder as a power source for pressurization, it is necessary to take account of the effects of combustion products such as combustion residues and combustion gases generated by the combustion. For example, in the case of syringes that use a powder as a source for pressurization of the injection solution, it is hygienically undesirable that the injection objective substance such as the injection solution as the object to be pressurized be contaminated by combustion products.

In the case where, as in the prior art, an elastically deformable membrane is used to separate the space in which the combustion of powder takes place and the space that accommodates an object to be pressurized and the energy of combustion of powder is transmitted to the object to be pressurized by the deformation of the membrane, the membrane is elastically deformed abruptly upon the combustion. In order to shift the object to be pressurized over a required distance by the pressurization, it is necessary for the membrane to deform by an amount adequate for the aforementioned required distance. In the prior art, to this end, it is necessary for the membrane to deform greatly toward the control member. Then, there is a risk that the membrane may be broken or torn. If the membrane is broken, it is difficult to confine the combustion products in the space in which the combustion takes place. Moreover, the intervenient membrane can prevent satisfactory transmission of the combustion energy to the control member.

Given the above-described problems, an object of the present disclosure, which pertains to a syringe that injects an injection objective substance such as an injection solution utilizing the combustion of powder, is to eliminate or reduce influences of the combustion products produced by the combustion of powder on the injection objective substance and to enable satisfactory transmission of the energy to the injection objective substance for injection.

Means for Solving the Problems

To solve the above problem, the present disclosure provides a structure in which a sealing member that separates the space an a main body of a syringe into an igniter side space and a first piston side space is adapted to confine combustion products produced by the igniter in the igniter side space. This structure can prevent contamination of the injection objective substance with the combustion products. Moreover, a portion of the sealing member that is in contact with the first piston part is shifted from an initial position on the igniter side of a fixed end portion of the sealing member to an ejection position on the syringe unit side of the fixed end potion by the combustion in the igniter. This configuration facilitates prevention of breakage of the sealing member while ensuring a satisfactorily large amount of shift of the first piston part.

Specifically, according to the present disclosure, there is provided a syringe used to inject an injection objective substance to an injection target area, comprising a syringe main body including a through-bore extending along the axial direction, a first piston part arranged in such a way as to be capable of sliding in said through-bore, a syringe unit disposed on the front end of said syringe main body and including a container chamber capable of containing said injection objective substance, a plunger that pressurizes said injection objective substance in said container chamber with sliding motion of said first piston part, and a nozzle part that has a fluid channel through which said injection objective substance pressurized by said plunger in said container chamber flows and ejects said injection objective substance from an ejection port provided at the end of said fluid channel, an igniter that causes powder to burn and applies ejection energy for ejecting said injection objective substance from said nozzle part to said first piston part by the combustion of powder in said igniter, and a sealing member that separates the space in said syringe main body into a first space in which said igniter is disposed and a second space in which said first piston part is disposed and confines combustion products produced by said igniter in said first space. Said first piston part has a plunger side end portion that is in contact with said plunger and a specific end portion including a specific end face that receives said ejection energy. Said sealing member has a fixed end portion fixed to an inner wall that defines the space in said syringe main body and a contact portion that is in contact with said specific end face of said specific end portion when the powder burns in said igniter. In a state before the combustion of powder in said igniter, said contact portion is located at an initial position on said igniter side of said fixed end portion. With the combustion of powder in said igniter, said contact portion shifts to an ejection position on said syringe unit side of said fixed end portion with sliding motion of said first piston part while being in contact with said specific end face.

In the syringe according to the present disclosure, the contact portion of the sealing member is shifted from the initial position to the ejection position by the ejection energy generated by the combustion of powder in the igniter. During the process of this shift, the contact portion is in contact with the specific end face of the first piston part, so that the first piston part slides in the through-bore. With the sliding motion of the first piston part, the plunger applies a pressure to the injection objective substance contained in the container chamber of the syringe unit, thereby ejecting the injection objective substance out of the syringe through the ejection port. So long as the shift of the contact portion of the sealing member caused by the combustion of powder, various structures may be employed, such as a structure in which the ejection energy is directly applied to the first piston part through the contact portion or a structure in which the ejection energy is firstly propagated to a gas, liquid, or solid and thereafter applied to the first piston part through the contact portion indirectly.

The injection objective substance contains a component expected to have some effects in the injection target area. Therefore, an accommodation state the injection objective substance in the syringe and a specific physical form of the injection objective substance such fluid in a liquid or gel form, powder, granular solid is not particularly limited as long as that the injection objective substance can be elected at least by the ejection energy. The injection objective substance may contain a component which is to be delivered to the injection target area of a living body as the target object. The component may exist in a state of being dissolved in the injection objective substance or may exist in a simply mixed state without being dissolved. Examples of the component to be delivered include vaccines for enhancing antibody, proteins for cosmetic treatments, and cultured cells for regenerating hair. These components are contained in fluid in a liquid or gel form so that the components can be injected, whereby the injection objective substance is formed. The syringe may supply the injection objective substance either through or not through a needle.

In the syringe according to the present disclosure, the igniter that causes powder to burn may be configured to ignite ignition charge accommodated in the igniter by an operation of the igniter thereby producing combustion products of the ignition charge or configured to induce further combustion of a known gas generating agent (e.g. a single base smokeless powder) by the ignition of the ignition charge thereby producing combustion products of the ignition charge and the gas generating agent. In the syringe according to the present disclosure, the structure of the igniter is not limited specifically.

As the powder burns in the igniter, the combustion products diffuse in the space in the syringe main body, and the ejection energy is transmitted to the first piston part generally by the pressure and heat. Such energy serves as a power source for ejection of the injection objective substance, as described above. Since the syringe according to the present disclosure is provided with the sealing member, such combustion products are confined in the first space and do not enter the second space. Thus, undesirable influences of the combustion products on the injection objective substance are eliminated. To achieve the sealing effect, it is necessary that the sealing member have an appropriate degree of resistance against the combustion of powder.

Moreover, it is undesirable that the provision or the sealing member interfere with the transmission of the ejection energy to the first piston part. Therefore, it is necessary for the sealing member to achieve both the satisfactory confinement of the combustion products and the satisfactory transmission of the ejection energy to the first piston part.

To achieve the above objects, the sealing member is configured in such a way that its contact portion shifts from the initial position on the igniter side of (in other words, closer to the igniter than) its fixed end portion fixed to the inner wall of the space in the syringe main body to the ejection position on the syringe unit side of (in other words, closer to the syringe unit than) the fixed end portion while in contact with the specific end face of the first piston part. With this configuration, after the combustion of powder, the sealing member deforms in such a way that the contact portion is turned inside out in relation to the fixed end portion, thereby propelling the sliding motion of the first piston part. Therefore, the sealing member is not expanded only in one direction with the combustion of powder, unlike in the case of prior arts. Therefore, the possibility of breakage of the sealing member is reduced. Moreover, with the aforementioned inside-out turning deformation structure, the range of shift of the contact portion with the sliding motion of the first piston part extends from the initial position on the igniter side of the fixed end portion to the ejection position on the syringe unit side of the fixed end portion. This eliminates a large deformation of the sealing member while ensuring a distance of shift of the contact portion large enough to enable the first piston part to slide over an adequate distance for electing the injection objective substance. Therefore, the sealing member is unlikely to interfere with the transmission of the ejection energy. This enables both the satisfactory confinement of the combustion products and the satisfactory transmission of the ejection energy to the first piston part.

In the syringe according to the present disclosure, the sealing member may be made of an elastic member. Then, the sealing member can expand with the combustion of powder in the igniter, enabling improved compatibility of the confinement of the combustion products and the transmission of the ejection energy to the first piston part.

The sealing member may further have an intermediate portion that extends between said fixed end portion and said contact portion and covers the side surface of said specific end portion extending along the sliding direction of said first piston part in the state before the combustion of powder in said igniter. Then, with the sliding motion of the first piston part resulting from the combustion of powder in said igniter, said contact portion shifts from said initial position to said election position while said intermediate portion expands in said sliding direction. With this design of the syringe, the contact portion shifts with the intermediate portion of the sealing member expanding in the sliding direction of the first piston part, while propelling the first piston part. This provides an additional amount of sliding of the first piston part corresponding to the amount of expansion. In consequence, the ejection energy generated by the combustion of powder is used preferably in propelling the first piston part, enabling the first piston part to slide over an adequate distance in pressurizing the injection objective substance. Moreover, as the intermediate portion that expands in the sliding direction of the first piston part is made of an elastic member, the intermediate portion can expand elastically. Therefore, the sealing member is unlikely to break.

In the above described syringe, the outer diameter of said specific end portion of said first piston part may be smaller than the inner diameter of said through-bore. Then, said intermediate portion expands in said sliding direction along the inner wall of said through-bore with the sliding motion of the first piston part resulting from the combustion of powder in said igniter. With this feature, the first piston part leaves a gap in the radial direction of the through-bore in the region near the specific end portion. When the contact portion moves with the combustion of powder, the intermediate portion can expand utilizing this gap, enabling smooth expansion of the intermediate portion. Therefore, the first piston part can slide over an adequate distance in pressurizing the injection objective substance, and breakage of the sealing member can be prevented.

The above-described syringe may further comprise a second piston part arranged in said first space in such a way as to be capable of sliding in said through-bore and to sandwich said contact portion of said sealing member with said specific end face of said first piston part. Said second piston part has an igniter side end portion opposed to said igniter to which said ejection energy is input and a first piston side end portion that transmits said ejection energy to said specific end face of said first piston part through said contact portion.

With this configuration of the syringe, the second piston part receives the ejection energy from the igniter by its igniter side end portion and transmits the ejection energy to the specific end face of the first piston part by its other end or the first piston side end portion through the contact portion of the sealing member sandwiched between the first piston part and the second piston part. Thus, the sealing member does not receive the election energy directly from the igniter but through the second piston part. Therefore, the contact portion is not exposed directly to high-temperature, high-pressure combustion products during the combustion of powder, and breakage of the sealing member including the contact portion can be prevented with improved reliability. Moreover, since the contact portion is sandwiched between the first piston part and the second piston part, a force for turning the sealing member inside out can be applied to the sealing member appropriately, enabling smooth sliding of the first piston part.

The present disclosure, which pertains to a syringe that injects an injection objective substance such as an injection solution utilizing the combustion of powder, enables elimination reduction of influences of the combustion products produced by the combustion of powder on the injection objective substance and satisfactory transmission of the energy to the injection objective substance for injection.

EMBODIMENTS

In the following, a needleless syringe 1 as an embodiment of the present disclosure will be described by way of example with reference to the accompanying drawings. The needless syringe 1 will be simply referred to as the syringe 1 hereinafter. It is to be understood that the embodiment will be described for illustrated purpose only, and the present disclosure is not limited to the embodiment described in the following.

First Embodiment

Figure 1A:
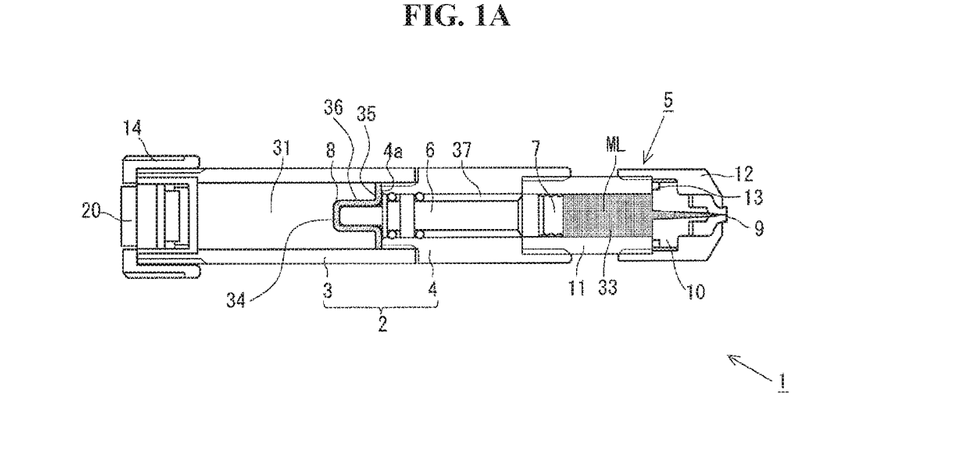
FIG. 1A is a cross sectional view of a syringe showing the general configuration of the syringe according to a first embodiment of the present disclosure.
Figure 1B:
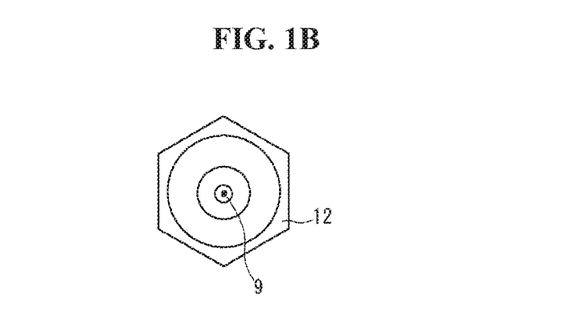
FIG. 1B is a first view of the syringe shown in FIG. 1A seen from a side of its nozzle part through which an injection solution is ejected.

FIG. 1A is a cross sectional view of the syringe 1, and FIG. 1B is a view of the syringe 1 seen from the side of its nozzle part 9 through which the injection solution is ejected. In the following description, the injection objective substance that is injected to an injection target area of a target object by the syringe 1 will be referred to as "injection solution". It should be noted, however, that the term "injection solution" is not intended to limit the content or the form of the substance to be injected. The component, which is to be delivered, for example, to a skin structure, may be either dissolved or not dissolved in the injection objective substance. Any specified form of the injection objective substance is available without any problem as well, for which various forms can be adopted, including, for example, liquid, gel form, or powder form, provided that the injection objective substance can be discharged to the skin structure from the nozzle part 9 by being pressurized.

The syringe 1 includes a syringe main body 2 made up of a first housing 3 and a second housing 4 and a syringe unit 5 disposed at the front end of the syringe main body 2 (i.e. the end of the second housing 4 opposite to its end connected to the first housing 3). The first housing 3 and the second housing 4 are fastened together by a screw. Inside the first housing 3, a combustion chamber 31 is formed. The combustion chamber 31 is the interior space extending in the axial direction of the first housing 3. Inside the second housing 4, a through-bore 37 is formed. The through-bore 37 is an interior space extending along the axial direction of the second housing 4. The combustion chamber 31 and the through-bore 37 are continuously arranged spaces inside the syringe main body 2, which are separated by a sealing member 8 that will be described later.

The syringe unit 5 provided at the front end of the syringe main body 2 includes a syringe unit main body 11 including an interior container chamber 33 in which injection solution ML is contained, a nozzle part 9 including a fluid channel through which the injection solution flows, and a nozzle holder 10 provided with the nozzle part 9. The nozzle holder 10 is attached to the syringe unit main body 11 by a holder cap 12 with a gasket 13 provided between the syringe unit main body 11 and the nozzle holder 10. The syringe unit main body 11 is mounted on the end of the second housing 4 of the syringe main body 2 by screwing. In the mounted state, the through-bore 37 inside the second housing 4 and the container chamber 33 inside the syringe unit main body 11 constitute a continuous space. In this mounted state, the injection solution ML is liquid-tightly contained in the container chamber 33 by a plunger 7, which is exposed to the through-bore 37. The plunger 7 is capable of sliding in the container chamber 33. As the plunger 7 slides in the container chamber 33, the plunger 7 applies pressure to the injection solution ML, so that the injection solution is ejected from the nozzle part 9. The plunger 7 is made of a rubber member that is thinly coated with silicone oil to allow smooth sliding in the container chamber 33.

Figure 2:
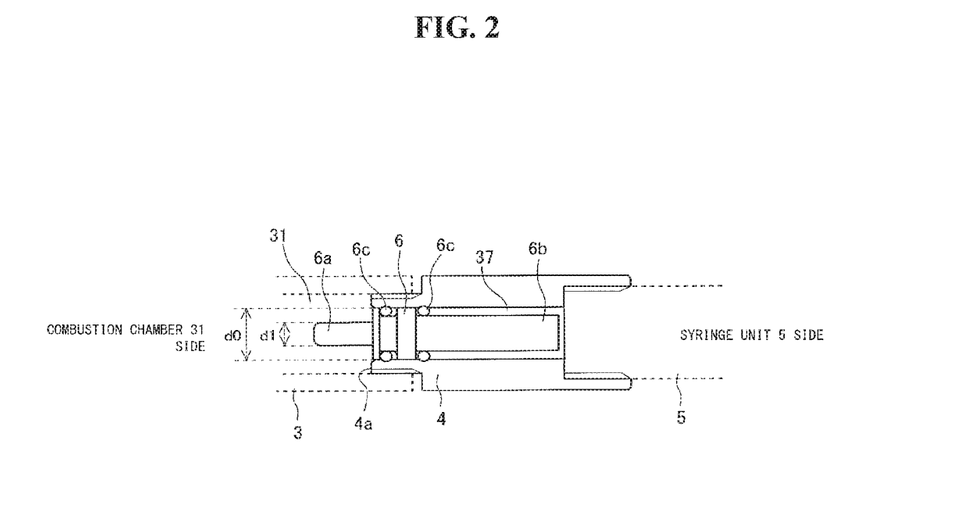
FIG. 2 is a diagram specifically showing a piston of the syringe shown in FIG. 1A.

A metal piston 6 is provided in the through-bore 37 inside the second housing 4 of the syringe main body 2. The piston 6 is held in the through-bore 37 in such a way as to be capable of sliding in the through-bore 37. FIG. 2 shows the details of the piston 6 to facilitate the understanding of its positional relationship with the second housing 4. The piston 6 has a generally shaft-like shape extending along the axial direction of the through-bore 37. The piston 6 has a first end portion 6a facing the combustion chamber 31 and a second end portion 6b facing the syringe unit 5, which is in contact with the plunger 7 provided in the syringe unit 5. O-rings 6c are provided around the piston 6 so as to allow the piston 6 to slide smoothly in the through-bore 37. In the state in which the first housing 3 (shown by broken lines in FIG. 2) and the second housing 4 are attached together to constitute the syringe main body 2 before the combustion of powder in an initiator 20 serving as an igniter (which will be described later), the first end portion 6a substantially projects into the combustion chamber 31 of the first housing 3 beyond the end face of the fitted portion 4a of the second housing 4 that is fitted into the combustion chamber 31. The aforementioned state will be hereinafter referred to as the "pre-ignition state". The diameter d1 of the first end portion 6a is smaller than the diameter d0 of the through-bore 37. Hence, when the piston 6 slides in the through-bore 37 toward the syringe 5, a gap is left between the side surface of the first end portion 6a (i.e. the surface of the piston 6 that extends along its axial direction) and the inner surface of the through-bore 37.

In the pre-ignition state shown in FIG. 1A, the sealing member 8 is attached to the end face of the fitted portion 4a of the second housing 4, which is a part of the inner wall of the syringe main body 2. Thus, the sealing member 8 made of an elastic material divides the space inside the syringe main body 2 into a space including the combustion chamber 31 on the initiator 20 side (corresponding to the first space according to the present disclosure) and a space including the through-bore 37 on the piston 6 side (corresponding to the second space according to the present disclosure) so as to confine the combustion products produced by the combustion of powder in the initiator 20 within the combustion chamber 31. The details of the structure of the sealing member 8 and its operation upon the combustion of powder in the initiator 20 will be described later.

Figure 3:
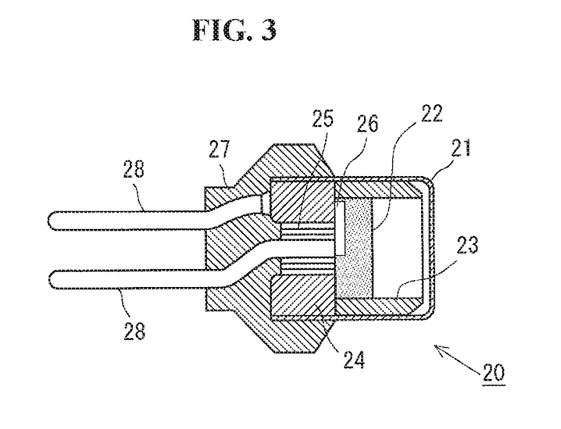
FIG. 3 is a diagram showing the basic structure of an initiator (or igniter) attached to the syringe shown in FIG. 1A.

Now, an exemplary structure of the initiator 20 will be described with reference to FIG. 3. The initiator 20 is an electric igniter. The initiator 20 has a cup 21, the surface of which is covered with an insulating cover. A space in which ignition charge 22 is set is defined inside the cup 21. In this space, a metal header 24 is also provided. An annular charge holder 23 is set on the top of the metal header 24. The charge holder 23 holds the ignition charge 22. On the bottom of the ignition charge 22 is arranged a bridge wire 26, which electrically connects one of two conducting pins 28 and the metal header 24. The two conducting pins 28 are fixed to the metal header 24 by an insulator 25 so that the two conducting pins 28 will be isolated from each other when a voltage is not applied. The opening of the cup 21 from which the two conducting pins 28 supported by the insulator 25 extend out is protected by a resin collar 27 with excellent isolation of the conducting pins 28 from each other.

With the above-described structure of the initiator 20, when a voltage is applied between the two conducting pins 28 by an external power source, a current flows through the bridge wire 26 to burn the ignition charge 22. Then, the combustion products produced by the combustion of the ignition charge 22 spout from the opening of the charge holder 23. An initiator cap 14 is formed to have a brim-shaped cross section so that the initiator cap 14 is caught or hooked by the outer surface of the initiator 20, and the initiator cap 14 is screw-fixed to the first housing 3. Thus, the initiator 20 is fixed to the first housing 3 by the initiator cap 14, and the initiator 20 is prevented from being disengaged from the syringe main body 2 due to the pressure generated upon ignition by the initiator 20.

Note that the ignition charge 22 used in the syringe 1 is preferably exemplified by a powder containing zirconium and potassium perchlorate (ZPP), a powder containing titanium hydride and potassium perchlorate (THPP), a powder containing titanium and potassium perchlorate (TiPP), a powder containing aluminum and potassium perchlorate (APP), a powder containing aluminum and bismuth oxide (ABO), a powder containing aluminum and molybdenum trioxide (AMO), a powder containing aluminum and copper oxide (ACO), a powder containing aluminum and ferric oxide (AFO), and a mixture of some of the aforementioned powders. Properties of these powders are that they generate a high-temperature, high-pressure plasma in the combustion immediately after the ignition, but the pressure drops quickly when the temperature drops to room temperature and the combustion products condense, because of the absence of gas components. Powders other than the aforementioned powders may also be used as the ignition charge.

In the case shown in FIG. 1A, the combustion chamber 31 is empty. However, a gas generating agent that is combusted by combustion products produced by the combustion of the ignition charge 22 to generate a gas may be provided in the combustion chamber 31. In the case where a gas generating agent is provided in the combustion chamber 31, it may be, for example, a single base smokeless powder including 98% by mass of nitrocellulose, 0.8% by mass of diphenylamine, 1.2% by mass of potassium sulfate. Alternatively, gas generating agents used in gas generators for airbags or seat belt pretensioners may be employed. In the case where such a gas generating agent is additionally employed, the drop rate of the generated pressure is lower, because gases generated by the combustion contain gas components even at room temperature unlike in the case where only the ignition charge 22 is employed. The combustion completion time, which is much longer than that of the ignition charge 22, can be varied by adjusting the dimensions, size, and shape, in particular surface shape of the gas generating agent provided in the combustion chamber 31. Thus, the pressure generated in the combustion chamber 31 can be adjusted appropriately by adjusting the amount, shape, and arrangement of the gas generating agent.

Figure 1C:
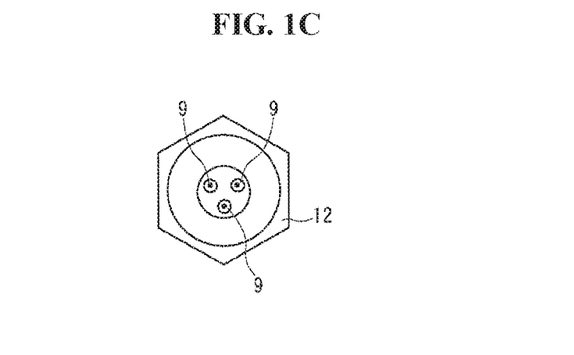
FIG. 1C is a second view of the syringe shown in FIG. 1A seen from a side of its nozzle part through which an injection solution is ejected.

The nozzle holder 10 may be provided with either one or plurality of nozzle parts 9. When a plurality of nozzle parts 9 are provided, fluid channels are provided for the respective nozzles in such a way that the injection solution ML released for the nozzles is delivered as uniformly as possible. In the case where a plurality of nozzle parts 9 are provided, it is preferred that the nozzle parts be arranged at regular intervals about the center axis of the syringe 1 as shown in FIG. 1C. The diameter of the fluid channel of the nozzle part 9 is smaller than the inner diameter of the through-bore 37. This makes the ejection pressure of the injection solution preferably high.

Now, the sealing member 8 in the pre-ignition state will be specifically described. As shown in FIG. 1A, the sealing member 8 is configured to cover the first end portion 6a of the piston 6 projecting into the combustion chamber 31. More specifically, the sealing member 8 includes a fixed end portion 35 that is attached to the fitted portion 4a of the second housing 4, a contact portion 34 that is in contact with the end face of the first end portion 6a and arranged to cover the end face, and an intermediate portion 36 that extends between the contact portion 31 and the fixed end portion 35 to cover the side surface of the first end portion 6a. Thus, in the cross section along the axial direction of the syringe 1 shown in FIG. 1A, the sealing member 8 has a U-shape, and the contact portion 34 constituting the "bottom" of the U-shape is located at its initial position that is closer to the initiator 20 than (or on the left of, in FIG. 1A) the fixed end portion 35.

Figure 4:
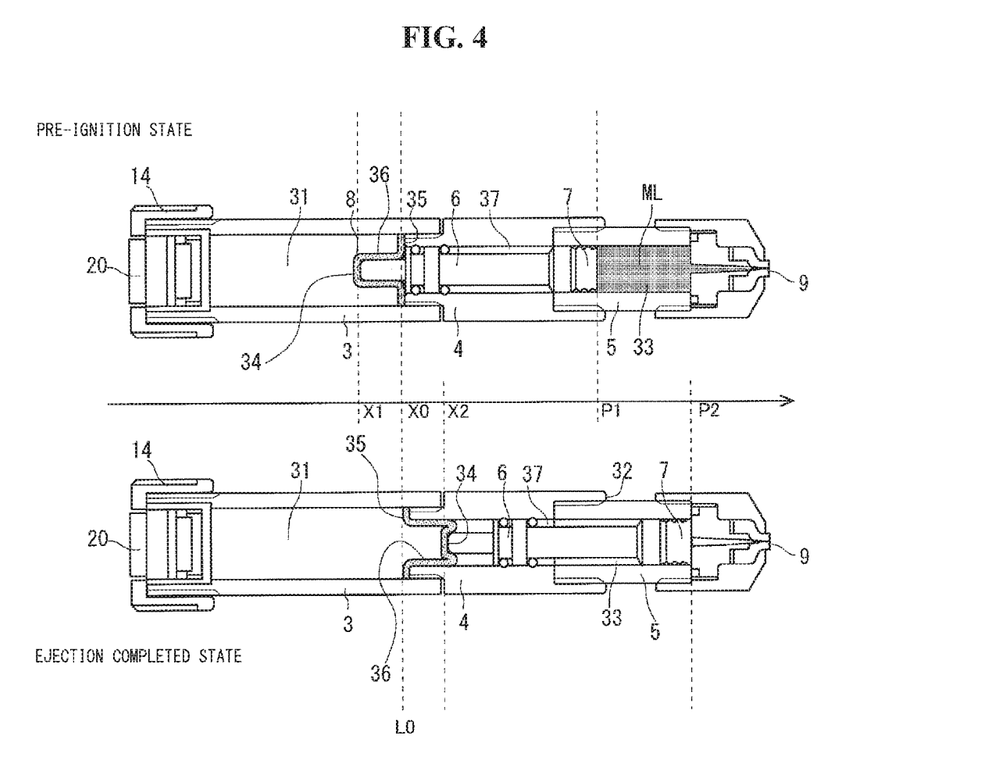
FIG. 4 is a diagram showing the syringe shown in FIG. 1A in a state before the combustion of powder in the initiator and a state after the combustion of powder is the initiator in comparison.

Next, the action of the sealing member 8 and the election of the injection solution with the syringe 1 upon the combustion of the ignition charge 22 in the initiator 20 will be described with reference to FIG. 4. The upper diagram in FIG. 4 shows the configuration of the syringe 1 in the pre-ignition state, and the lower diagram in FIG. 4 shows the syringe 1 in the state after ejection of the injection solution caused by the combustion of the ignition charge 22 has been completed. The latter state will be hereinafter referred to as the "ejection completed state". In FIG. 4, the positions of the fixed end portion 35 of the sealing member 8 in the diagrams showing the pre-ignition state and the election completed state are aligned with respect to the axial direction of the syringe 1 for of the two states. The position of the fixed end portion 35 that is common between the two states is indicated as position X0, and a fiducial line at position X0 is indicated as line L0.

The position of the contact portion 34 in the pre-ignition state is indicated by X1, which is on the initiator 20 side of (in other words, closer to the initiator 20 than) position X0, as described above. The position of the plunger 7 in this state is indicated by P1. As the ignition charge 22 burns, combustion products diffuse in the combustion chamber 31, so that the pressure in the combustion chamber 31 rises. Consequently, the pressure is exerted on the sealing member 8 also. In particular, the pressure that pushes the piston 6 in the direction toward the syringe unit 5 is the pressure that acts on the piston 6 through the contact portion 34 of the sealing member 8. Therefore, the end face of the first end portion 6a of the piston 6 in contact with the contact portion 34 is the surface that receives the election energy from the initiator 20.

As above, the contact portion 34 of the sealing member 8 is a portion that transmits the ejection energy generated by the combustion of the ignition charge 22 to the piston 6. Thus, as the contact portion 34 of the sealing member 8 moves toward the syringe unit 5, the piston 6 slides in the through-bore 37. As the piston 6 slides, the plunger 7 pushes the injection solution ML, so that the injection solution ML is ejected to the injection target area through the nozzle part 9. In the ejection completed state in which the ejection of the injection solution ML has been completed, as shown in the lower drawing in FIG. 4, while the contact portion 34 is in contact with the end face of the first end portion 6a of the piston 6, the plunger 7 abuts the inner surface of the nozzle holder 10 provided with the nozzle 9, and therefore the sliding shift of the piston 6 is restricted. In this state, the contact portion 34 is located at a position indicated by X2 (referred to as the ejection position), which is closer to the syringe unit 5 than position X0. The position of the plunger 7 is indicated by P2.

In the syringe 1 as above, during the combustion of the ignition charge 22, the contact portion 34 of the sealing member 8 shifts from the initial position X1 assumed in the pre-ignition state to the ejection position X2 assumed in the ejection completed state. The distance (X2−X1) of this shift of the contact portion 34 is equal to the distance (P2−P1) of shift of the plunger 7 for ejection of the injection solution ML. With this shift, the sealing member 8 deforms in such a way as to be turned inside out. The shift distance of the piston 6 and the plunger 7 that is needed to eject the injection solution ML is achieved by this inside-out turning deformation of the sealing member 8. In this inside-out turning deformation of the sealing member 8, it is not necessary for the sealing member 8 to elastically deform greatly, but this inside-out turning deformation is basically achieved only by a shift of the intermediate portion 36 and the contact portion 34 of the sealing member 8 with the fixed end portion 35 being fixed. Even in cases where the contact portion 34 shifts greatly toward the syringe unit 5 due to the ejection energy generated by the combustion of the ignition charge 22 to cause the intermediate portion 36 to expand, the intermediate portion 36 firstly shifts from the state shown in the upper drawing in FIG. 4 toward the syringe unit 5 and thereafter expands with the shift of the contact portion 34. Therefore, the amount of elastic deformation of the intermediate portion 36 can be kept small. Therefore, breakage of the sealing member 8 can be prevented while ensuring a sufficient distance of shift of the plunger 7 for ejecting the injection solution ML. Thus, the sealing member 8 can continue to provide satisfactory protection against contamination of the injection solution with combustion products.

As described above, the diameter d1 of the first end portion 6a of the piston 6 is smaller than the inner diameter d0 of the through-bore 37. Therefore, as the aforementioned inside-out turning deformation of the sealing member 8 progresses, the intermediate portion 36 partly gets into the gap between the first end portion 6a and the wall of the through-bore 37, so that the inside-out turning deformation and expansion of the intermediate portion 36 can progress smoothly along the inner wall of the through-bore 37. When at the ejection position, the contact portion 34 is not necessarily in contact with the end face of the first end portion 6a of the piston 6, but the contact portion 34 may be detached from the end face of the first end portion 6a when it comes to the ejection position, so long as it causes the piston 6 to slide for ejection of the injection solution ML.

Second Embodiment

Figure 5:
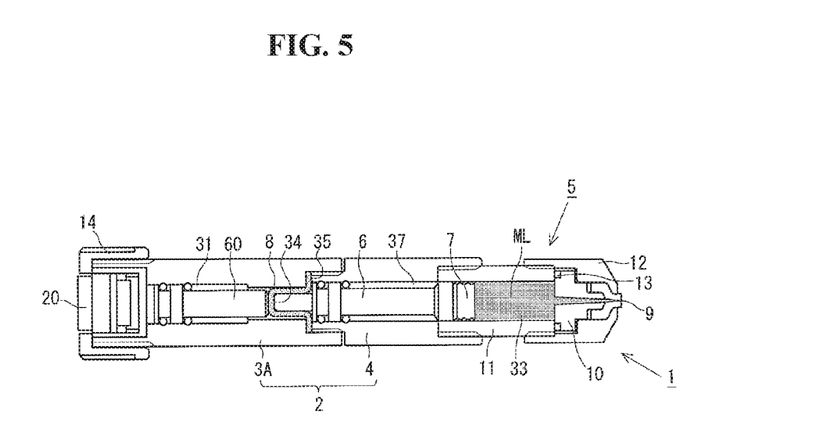
FIG. 5 is a diagram showing the general configuration of a syringe according to a second embodiment of the present disclosure.

FIG. 5 shows a second embodiment of the present disclosure. In the above-described first embodiment, the ejection energy generated by the initiator 20 is transmitted to the piston 6 through the sealing member 8, and the sealing member 8 is directly exposed to the combustion gases. In the second embodiment, the ejection energy is firstly transmitted to a piston 60, and then indirectly transmitted to a piston 6 through a sealing member 8. Thus, the sealing member 8 is prevented from being exposed directly to combustion products. In this second embodiment, a syringe main body 2 is made up of a first housing 3A and a second housing 4. In the following description, components in the second embodiment that are substantially the same as those in the first embodiment will be denoted by the same reference numerals and will not be described in further detail.

The first housing 3A has a combustion chamber 31 formed inside. The combustion chamber 31 is configured in such a way that combustion products produced by the initiator 20 diffuse in it. The piston 60 made of metal is provided in the combustion chamber 31. The piston 60 is held in such a way as to be capable of sliding in the combustion chamber 31. One end of the piston 60 is opposed to the initiator 20, and the other end is arranged to sandwich the contact portion 34 of the sealing member 8 with the first end portion 6a of the piston 6. When the ignition charge 22 is burned by the operation of the initiator 20, the ejection energy is input to the end of the piston 60 opposed to the initiator 20, and then transmitted to the piston 6 through the contact portion 34 of the sealing member 8. Thus, when the ignition charge 22 burns, the piston 6 slides along with the piston 60. In this case also, the sealing member 8 undergoes an inside-out turning deformation like in the above-described first embodiment. In this second embodiment, since the contact portion 34 is sandwiched between the piston 60 and the piston 6, the deformation of the sealing member 8 is restricted to a specific direction, enabling the inside-out turning deformation to progress smoothly. In this embodiment, since the election energy is firstly input to the piston 60, the sealing member 8 is prevented from being exposed directly to the combustion products. This reduces the thermal stress on the sealing member 8, enabling improved prevention of its breakage.

Example 1

We conducted an experiment to examine whether sealing is achieved by the sealing member 8 when powder is burned in the initiator 20 in the syringe 1 according to the above-described first embodiment. The rubber material used as the sealing member 8 was NBR (nitrile-butadiene rubber). The examination was carried out using rubber materials having different hardness (or durometers) at different temperatures of the syringe 1 at the time of operation, and breakage or the like of the sealing member 8 was checked visually.

More specifically, the examination was carried out using two rubber materials having durometers of 50 and 70 at three different temperatures of the syringe 1, specifically high temperature (50° C.), normal temperature (20° C.), and low temperature (0° C.) The peak pressure in the combustion chamber 31 during the combustion of powder was 30 MPa, and the thickness of the sealing member 8 was 1 mm. For each hardness and temperature, the combustion of powder in the initiator 20 was performed three times, and breakage of the sealing member 8 was checked, but no breakage was found in all the conditions.

Example 2

We conducted an experiment to examine whether sealing is achieved by the sealing member 8 when powder is burned in the initiator 20 in the syringe 1 according to the above-described second embodiment. The rubber materials used as the sealing member 8 were chloroprene and NBR. The examination was carried out at different temperatures of the syringe 1 at the time of operation, and breakage or the like of the sealing member 8 was checked visually.

More specifically, the examination was carried out using a chloroprene having a durometer of 65 and an NBR having a durometer of 70 as rubber materials at three different temperatures of the syringe 1, specifically high temperature (50° C.), normal temperature (20° C.), and low temperature (0° C.) The peak pressure in the combustion chamber during the combustion of powder was 30 MPa, and the thickness of the sealing member 8 was 1 mm. For each rubber material and temperature, the combustion of powder in the initiator 20 was performed three times, and breakage of the sealing member 8 was checked, but no breakage was found in all the conditions.

It will be understood from the above examples that NBR can be preferably used as the rubber material of the sealing member 8 in both the embodiments. In the second embodiment, chloroprene can also be used as the material of the sealing member 8. The above examples are given merely by way of example. Chloroprene can be used as the rubber material of the sealing member in the first embodiment also with appropriate adjustment of the hardness thereof and appropriate limitation of the temperature condition of the syringe 1.

OTHER EXAMPLES

According to the syringe 1 of the present disclosure, for example, cultured cells, stem cells, and the like may be seeded or inoculated into injection target cells or scaffold tissues (scaffolds) in the field of the regenerative medicine of human, in addition to the case where the injection liquid is injected into the skin structure. For example, as described in Japanese Patent Application Publication No. 2008-206477, the syringe 1 may inject cells which may be appropriately determined by those skilled in the art depending on a transplantation portion and the purpose of the cell regeneration, for example, endothelial cells, endothelial precursor cells, myeloid cells, preosteoblast, chondrocytes, fibroblast, skin cells, muscle cells, liver cells, kidney cells, intestinal tract cells, and stem cells, as well as all cells considered in the field of the regenerative medicine. Practically, cells are injected into an implantation site for implantation by pressurizing a liquid containing cells to be seeded (cell suspension) contained in the container chamber 33.

Further, the syringe 1 of the present disclosure may be also used for delivering DNA or the like to cells or scaffold tissues (scaffolds) as described in Japanese Translation of PCT International Application Publication No. 2007-525192. In this case, it is possible to suppress an adverse effect on cells themselves or scaffold tissues (scaffolds) themselves when the syringe 1 of the present disclosure is used, as compared with when the delivery is performed using a needle. Therefore, it can be said that the use of the syringe 1 is more desirable.

Further, the syringe 1 of the present disclosure is ideally useful, for example, when various genes, cancer inhibiting cells, lipid envelops, and the like are directly delivered to target tissues and when antigen genes are administered to enhance the immunity against pathogens. In addition to the above, the syringe 1 can be also used, for example, in the field of medical treatment for various diseases (for example, see Japanese Translation of PCT International Application Publication Nos. 2008-508881 and 2010-503616) and the field of immunological medical treatment (for example, see Japanese Translation of PCT International Application Publication No. 2005-523679). The field, in which the syringe 1 is usable, is not intentionally limited.

The invention claimed is:

1. A syringe used to inject an injection objective substance to an injection target area, comprising:
   a syringe main body including a through-bore extending along the axial direction;

a first piston part arranged in such a way as to be capable of sliding in said through-bore;

a syringe unit disposed on the front end of said syringe main body and including a container chamber capable of containing said injection objective substance, a plunger that pressurizes said injection objective substance in said container chamber with sliding motion of said first piston part, and a nozzle part that has a fluid channel through which said injection objective substance pressurized by said plunger in said container chamber flows and ejects said injection objective substance from an ejection port provided at an end of said fluid channel;

an igniter that causes powder to burn and applies ejection energy for ejecting said injection objective substance from said nozzle part to said first piston part by a combustion of powder in said igniter; and a sealing member that separates a space in said syringe main body into a first space in which said igniter is disposed and a second space in which said first piston part is disposed and confines combustion products produced by said igniter in said first space, wherein said first piston part has a plunger side end portion that is in contact with said plunger and a specific end portion including a specific end face that receives said ejection energy, said sealing member has a fixed end portion fixed to an inner wall that defines the space in said syringe main body and a contact portion that is in contact with said specific end face of said specific end portion when the powder burns in said igniter, in a state before the combustion of powder in said igniter, said contact portion is located at an initial position on an igniter side with respect to said fixed end portion, and with the combustion of powder in said igniter, said contact portion shifts to an ejection position on a syringe unit side with respect to said fixed end portion with sliding motion of said first piston part while being in contact with said specific end face, wherein said fixed end portion is disposed between the initial position and the ejection position.

2. A syringe according to claim 1, wherein said sealing member is made of an elastic material.

3. A syringe according to claim 2, wherein said sealing member further has an intermediate portion that extends between said fixed end portion and said contact portion and covers a side surface of said specific end portion extending along a sliding direction of said first piston part in the state before the combustion of powder in said igniter, and with the sliding motion of the first piston part resulting from the combustion of powder in said igniter, said contact portion shifts from said initial position to said ejection position while said intermediate portion expands in said sliding direction.

4. A syringe according to claim 3, wherein an outer diameter of said specific end portion of said first piston part is smaller than an inner diameter of said through-bore, and said intermediate portion expands in said sliding direction along the inner wall of said through-bore with the sliding motion of the first piston part resulting from the combustion of powder in said igniter.

5. A syringe according to claim 1, further comprising a second piston part arranged in said first space in such a way as to be capable of sliding in said through-bore and to sandwich said contact portion of said sealing member with said specific end face of said first piston part, said second piston part including an igniter side end portion opposed to said igniter to which said ejection energy is input and a first piston side end portion that transmits said ejection energy to said specific end face of said first piston part through said contact portion.

6. A syringe according to claim 1, wherein said sealing member physically separates said first space from said second space such that the combustion products produced by said igniter in said first space do not contact said specific end face of said specific end portion of said first piston part.

7. A syringe according to claim 1, wherein said sealing member is configured to deform in such a way as to be turned inside out when said contact portion shifts to the ejection position.

8. A syringe according to claim 7, wherein a portion of said sealing member maintains a concave shape facing said first piston part when said sealing member is turned inside out.

* * * * *

UNITED STATES PATENT AND TRADEMARK OFFICE
CERTIFICATE OF CORRECTION

PATENT NO. : 10,549,038 B2
APPLICATION NO. : 15/638211
DATED : February 4, 2020
INVENTOR(S) : Yuzo Yamamoto et al.

Page 1 of 1

It is certified that error appears in the above-identified patent and that said Letters Patent is hereby corrected as shown below:

In the Specification

Column 2, Line 21, delete "an a" and insert --in a--.

Column 3, Line 17, delete "member" and insert --member is--.

Column 3, Line 26, delete "state" and insert --state of--.

Column 3, Line 30, delete "elected" and insert --ejected--.

Column 4, Line 1, delete "or" and insert --of--.

Column 4, Line 31, delete "electing" and insert --ejecting--.

Column 5, Line 47, delete "reduction" and insert --or reduction--.

Column 6, Line 3, delete "is" and insert --in--.

Column 9, Line 13, delete "31" and insert --34--.

Column 9, Line 21, delete "election" and insert --ejection--.

Column 9, Line 32, delete "election" and insert --ejection--.

Column 9, Line 51, delete "election" and insert --ejection--.

Column 11, Line 25 (approx.), delete "election" and insert --ejection--.

Signed and Sealed this
Twenty-fifth Day of August, 2020

Andrei Iancu
*Director of the United States Patent and Trademark Office*